United States Patent [19]

Rosen et al.

[11] Patent Number: 4,844,891
[45] Date of Patent: Jul. 4, 1989

[54] ADMIXTURES OF IODOPROPARGYL COMPOUNDS AND A FORMALDEHYDE DONOR

[75] Inventors: Marvin Rosen, Totowa; Kenneth J. Iandoli, Hawthorne, both of N.J.

[73] Assignee: Lonza, Inc., Fair Lawn, N.J.

[21] Appl. No.: 151,702

[22] Filed: Feb. 3, 1988

[51] Int. Cl.$^4$ .................. A61L 13/00; C11D 3/48
[52] U.S. Cl. .................. 424/76.4; 252/106; 252/107; 252/8.6; 424/70; 422/36; 422/37; 514/244; 514/389
[58] Field of Search .............. 252/106, 107, DIG. 13; 106/18.35, 18.32; 514/389, 244; 422/37, 36; 424/76.4

[56] References Cited

U.S. PATENT DOCUMENTS

| | | | |
|---|---|---|---|
| 3,228,829 | 1/1966 | Wolf et al. | 514/244 |
| 3,830,913 | 8/1974 | Harich | 424/195 |
| 3,923,870 | 12/1975 | Singer | 560/148 |
| 4,172,140 | 10/1979 | Shull et al. | 252/51.5 A |
| 4,202,882 | 5/1980 | Schwartz | 514/244 |
| 4,323,602 | 4/1982 | Parker | 427/298 |
| 4,496,576 | 1/1985 | Loncrini et al. | 514/389 |
| 4,655,815 | 4/1987 | Jakubowski | 71/67 |

FOREIGN PATENT DOCUMENTS 0091740 10/1983 European Pat. Off. .
960732 6/1964 United Kingdom .

Primary Examiner—Prince E. Willis
Attorney, Agent, or Firm—Bert J. Lewen; Henry Sternberg

[57] ABSTRACT

A broad spectrum preservative composition which comprises (a) a formaldehyde donor and (b) a halopropynyl compound; formulations containing such compositions, particularly personal care and household products; and a method of inhibiting the growth of microorganisms which includes contacting said microorganisms with the preservative composition.

10 Claims, No Drawings

ADMIXTURES OF IODOPROPARGYL COMPOUNDS AND A FORMALDEHYDE DONOR

BACKGROUND OF THE INVENTION

The need for effective and economical preservative compositions is well known. There are a wide variety of applications where inhibiting the growth of microorganisms is necessary, as for example personal care products such as shampoos, creams, lotions, cosmetics, soaps and household products such as laundry detergents, hard surface cleaners, and fabric softeners. The shelf life of these preparations depends on their resistance to microbial spoilage.

In addition, in many industrial applications, antimicrobial agents are useful in paint, wood, textiles, adhesives, sealants, leather, rope, paper pump, plastics, fuel, oil, and rubber and metal working fluids. The control of slime-producing bacteria and fungi in pump and paper mills and cooling towers is a matter of substantial commercial importance.

Certain compounds have long been known to be useful as preservatives. For example, U.S. Pat. No. 3,987,184 shows the use of 1,3-dimethylol-5,5-dimethylhydantoin (DMDMH) as a useful formaldehyde donor for the preservation of personal care products, cosmetics, and household and industrial products. While it is inexpensive and effective against a wide variety of bacteria, the rate of kill is slow in inhibiting fungi and yeasts.

On the other hand, compounds such as the halopropynyl carbamates are known for their fungicidal activity; however, they are extremely costly and, as a result, have only found applications in specialty areas where high costs can be justified.

Other commercially known preservatives include Quaternium-15 (Dowicil 200, a trademark of Dow Chemical Company). It has the disadvantage of being a solid product which must be solubilized in water before it can be used in the end product. In aqueous solution it exhibits pH drift and causes formulation problems, particularly with regard to viscosity and color.

Imidazolidinyl urea (Germall 115, a trademark of Sutton Laboratories) has virtually no fungicidal activity. The manufacturer of this product actually recommends that it be used with parabens to provide fungicidal action.

Formaldehyde in the free state, as in formalin, is effective only for short periods of time. In addition, it is inactivated by protein.

Admixtures of methylchloroisothiazolinone and methylisothiazolinone (Kathon CG, a trademark of Rohm & Haas) are unstable in the presence of organic sulfur compounds, ingredients commonly used in personal care products. They react also with peroxide impurities present in materials such as amine oxides.

2-Bromo-2-nitropropane-1,3-diol (Lexgard Bronopol, a trademark of Inolex) has limited fungicidal activity and parabens are required to provide microbiological activity.

Alkyl parabens (e.g., methyl, ethyl and propyl) have limited bactericidal action. They are generally solubilized in oil since they are poorly soluble in water, leading to formulation difficulties for personal care and household products. They are often inactivated by commonly used materials such as gelatin, methyl cellulose, and polyethylene glycol.

The development of an effective synergistic combination, inexpensive in price and having a broad spectrum activity, has long been sought. For example, in U.S. Pat. No. 4,454,146, a preservative composition having two components (the first being benzoic acid, formaldehyde or a mixture of isothiazolinone and a second component containing compounds with condensed aromatic rings) has been suggested for preservative applications. In addition, U.S. Pat. No. 3,699,231 describes a synergistic mixture of sodium dimethyldithiocarbamate and formaldehyde for killing bacteria in drilling fluids; U.S. Pat. No. 3,929,561 comprises mixtures of isothiazolinones and bis(trichloromethyl) sulfones for inhibiting the growth of slime for industrial purposes; and U.S. Pat. No. 4,655,815 describes synergism between 2-bromo-2-bromomethylglutaronitril and a formaldehyde donor such as dimethyloldimethylhydantoin, hydroxyaminopropanol, hydroxyethylnitropropanediol, blends of hydroxymethyl azadioxabicyclooctane and hydroxymethylamino ethanol; chloroallyl triazoadamantine chloride, chloroallyl heximinium chloride and hexamethylene tetramine halo hydrocarbon quaternaries.

Unfortunately, the above compositions are not suitable for personal care and household products because of their unfavorable toxicity, particularly skin and eye irritation and/or incompatibility with commonly used ingredients.

BRIEF DESCRIPTION OF THE INVENTION

In accordance with the invention, it has now been discovered that synergistic combination of a selected formaldehyde donor and an iodopropargyl compound give both broad spectrum bactericidal and fungicidal activity suitable for use in personal care and household products. A particularly surprising aspect of the discovery is that an extremely small amount of the costly halopropynyl carbamate can be combined with the formaldehyde donor to give a composition that has particularly outstanding fungicidal activity. This activity could in no way be predicted based on the known biocidal effects of the components individually.

Relative proportions of the two components can vary widely and the optimum proportion would be affected by the various compounds selected as well as the desired application. It has been discovered that a total composition which contains as little as 1 part in 50 of the costly iodopropargyl compound will have a fungicidal activity exceeding that of an equal weight of the halopropynyl carbamate alone. This is particularly surprising since this enhancement is realized with formaldehyde donors which have essentially no fungicidal activity.

DETAILED DESCRIPTION OF THE INVENTION

The first component of the synergistic composition of the invention may be selected from the known formaldehyde donors having chemical and physical characteristics compatible with use in personal care products. Such products must, of course, not be odiferous or an irritant or toxic when applied to the skin. Examples of such compounds include dimethyloldimethyldantoin, N,N''-methylene bis [N'-[hydroxymethyl)-2,5-dioxo-4-imidazolidinyl]urea]and N-(hydroxymethyl)-N-(1,3-dihydroxymethyl-2,5-dioxo-4-imidazolidinyl)-N'-(hydroxymethyl) urea; the cis isomer of 1-(3-chloroallyl)-3,5,7-triaza-1-azoniaadamantane chloride.

Examples of compounds which may be used as the second component of the invention are the fungicidally active iodopropargyl derivatives. These include compounds derived from propargyl or iodopropargyl alcohols such as the esters, ethers, acetals, carbamates and carbonates and the iodopropargyl derivatives of pyrimidines, triazolinones, tetrazoles, triazinones, sulfamides, benzothiazoles, ammonium salts, carboxamides, hydroxamates, and ureas. Preferred among these compounds is 3-iodo-2-propynylbutyl carbamate, IPBC. This compound is included within the broadly useful class of compounds having the generic formula:

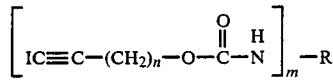

wherein R is selected from the group consisting of substituted and unsubstituted alkyl, aryl and alkylaryl groups having from 1 to 20 carbon atoms, and m and n are independent integers from 1 to 3.

As noted above, the ratio of the two components varies depending on the application and the particular component selected. Broadly speaking, from 50:1 to 1:1 parts of the first to the second component may be used, preferably from 30:1 to 2:1, most preferably from 20:1 to 10:1, the parts being by weight.

The compositions of the invention have been found effective to inhibit the growth of bacteria, fungi and yeasts. Specifically, fungi and yeasts which may be inhibited include *Aspergillus niger, Candida albicans, Lentinus lepideus, Gloeophyllum trabeum, Corioulus yersicolor, Trichoderma viride, Alternaria alternata, Pencillium decumbens, Botrytis cinerea, Colletotrichum coffeanum, Verticillium dahliae,* and *Trichophyton mentagrophytes.* Examples of the bacteria include *Salmonella choleraesuis, Serratia marcescens, Klebsiella pneumoniae, Enterobacter aerogenes, Aerobacter aerogenes, Bacillus subtilis, Proteus vulgaris, Streptcoccus faecalis, Pseudomonas aeruginosa, Escherichia coli,* and *Staphylococcus aureus.*

The incorporation of the composition of the invention into personal care and household products is done in accordance with standard practices.

Typical personal care formulations, in addition to those described in the Examples, are set forth in the following tables:

| Personal Care Product Traditional All-Purpose Shampoo | | |
|---|---|---|
| Ingredient | Percent (Wt) | Functionality |
| Sodium lauryl sulfate | 35.00 | Surfactant |
| Cocodiethanolamide | 4.00 | Viscosity builder |
| Sodium chloride | 0.80 | |
| Citric acid | 0.17 | |
| Preservative | q.s. | |
| Water, deionized | 60.03 | |

The shampoo is prepared by dissolving the citric acid, sodium chloride, sodium lauryl sulfate and preservative in water and then adding the cocodiethanolamide, while stirring to insure homogeneity.

| Personal Care Product Shampoo | | |
|---|---|---|
| Ingredient | Percent (Wt) | Functionality |
| Sodium lauryl ether (2) sulfate | 35.0 | Surfactant |
| TEA lauryl sulfate | 25.0 | Surfactant |
| Cocodiethanolamide | 3.0 | Foam booster |
| Hydrolyzed animal protein | 1.0 | Conditioner |
| Preservative | q.s. | |
| Water, deionized | 36.0 | |

To formulate this shampoo, all of the ingredients except the preservative are added to water and heated to 65° C. The preservative is added to achieve a clear solution while cooling to room temperature with stirring. If needed, the pH is adjusted to 7.0 with 50% citric acid and triethanolamine.

| Personal Care Product Baby Shampoo | | |
|---|---|---|
| Ingredient | Percent (Wt) | Functionality |
| Cocoamphocarboxyglycinate, sodium lauryl sulfate, and sodium laureth sulfate | 20.0 | Amphoteric surfactants and concentrates |
| Cocoamphocarboxyglycinate | 10.0 | Amphoteric surfactant |
| Sorbitan monolaurate (20) POE | 5.0 | Eye irritation mitigant |
| Polyethylene glycol 6000 distearate | 1.3 | Viscosity builder |
| Citric acid | 0.3 | |
| Preservative | q.s | |
| Water, deionized | 63.36 | |

In making this shampoo, the citric acid is dissolved in the water, the mixture heated and the remaining ingredients added in the order given. Polyethylene glycol 6000 distearate is dissolved at 75° C. The mixture is stirred while allowing it to cool to room temperature. The preservative is added at room temperature.

| Personal Care Product Cationic Hair Conditioner | | |
|---|---|---|
| Ingredient | Percent (Wt) | Functionality |
| Stearyldimethylbenzyl-ammonium chloride | 8.0 | Conditioner |
| Hydrogenated starch hydrolysate | 3.0 | Humectant |
| Glyceryl monostearate, s.e. | 1.0 | Emulsifier, opacifier |
| Sorbitan tristearate (20) POE | 0.5 | Emulsifier |
| Potassium chloride | 0.4 | |
| Preservative | q.s. | |
| Water, deionized | 87.1 | |

In this formulation, half of the water is heated to 70° C. and the glyceryl monostearate and POE-20 sorbitan tristearate are added with stirring. The quaternary salt, preheated to 70° C., and the hydrogenated starch hydrolysate are added and stirring continued for 15–30 minutes. In a separate vessel, the potassium chloride is dissolved in the remainder of the water, heated to 65° C. and added to the rest of the batch. The emulsion is allowed to cool slowly to 40° C. with agitation.

| Personal Care Product Conditioning Hair Mousse | | |
|---|---|---|
| Ingredient | Percent (Wt) | Functionality |
| Acetamide MEA | 5.0 | Lubricant |
| Stearalkonium chloride | 4.5 | Conditioner |
| Sodium lauryl sulfate | 3.5 | Emulsifier |
| Hydrogenated starch hydrolysate | 5.0 | Humectant |
| Polyquaternium-11 | 4.0 | Holding power |
| Polyquaternium-10 | 0.7 | Holding power |
| Lauryl alcohol (23) ethoxylate | 0.5 | Solubilizer |
| Preservative | q.s. | |
| Water, deionized | 76.5 | |

The Polyquaternium-10 is dispersed in water with mild agitation and heated to 70° C. The stearalkonium chloride, sodium lauryl sulfate, hydrogenated starch hydrolysate, Polyquaternium-11 and the ethoxylated lauryl alcohol are added one at a time and mixed well after addition. The blend is cooled with mild agitation and the preservative added.

| Personal Care Product Water Repellent Sunscreen | | |
|---|---|---|
| Ingredient | Percent (Wt) | Functionality |
| Phase A | | |
| Myristyl propionate | 2.0 | Emollient |
| Silicone fluid | 10.0 | Repellent |
| Octyl dimethyl p-aminobenzoic acid | 5.0 | Sunscreen |
| Glyceryl stearate | 1.5 | Emulsifier, opacifier |
| Stearic acid, triple pressed | 3.5 | Emulsifier for soap |
| Mink oil | 5.0 | Skin conditioner |
| Phase B | | |
| Hydrogenated starch hydrolysate | 5.0 | Humectant |
| Triethanolamine | 1.0 | Emulsifier for soap |
| Preservative | q.s. | |
| Water, deionized | 66.7 | |

The ingredients for Phases A and B, without the preservative are mixed in separate vessels. The phases are melted at 75° C., and mixed by adding Phase B slowly to Phase A with stirring. The mixture is cooled to room temperature while the stirring is continued. The preservative is added during the cooling cycle.

The following are examples of household products:

| Household Product Light Duty Liquid Detergent | | |
|---|---|---|
| Ingredient | Percent (Wt) | Functionality |
| Sodium lauryl ether sulfate (60%) | 14.50 | Surfactant |
| Sodium linear alkyl sulfonate (60%) | 28.50 | Surfactant |
| Cocodiethanolamide | 4.50 | Viscosity builder |
| Citric acid (50%) | 0.15 | |
| Preservative | q.s. | |
| Water, deionized | 52.35 | |

The ingredients are combined with water in the order listed and stirred after the addition of each until a clear solution is formed.

| Household Product Fine Fabric Detergent | | |
|---|---|---|
| Ingredient | Percent (Wt) | Functionality |
| Myristamine oxide | 5.00 | Foam booster |
| Cocodiethanolamide | 2.00 | Viscosity foam booster |
| Sodium linear alkylate sulfonate, 60% | 15.00 | Surfactant |
| Sodium alpha olefin sulfonate, 40% | 25.00 | Surfactant |
| Citric acid, anhydrous | 0.25 | |
| Preservative | q.s. | |
| Water | 52.75 | |

The citric acid is dissolved in the water and, with agitation, the remaining ingredients added in the order listed until the product is homogeneous.

| Household Product Fabric Softener | | |
|---|---|---|
| Ingredient | Percent (Wt) | Functionality |
| Ditallowdiamido methosulfate or Ditallowdimethyl ammonium chloride | 4.0 4.0 | Softener |
| PEG stearate 400 | 1.5 | Emulsifier and opacifier |
| Preservative | q.s. | |
| Water | 96.0 | |

The quaternary salts, the preservatives and the water are mixed until homogeneous.

| Household Product Solid Gel Room Deodorizer | | |
|---|---|---|
| Ingredient | Percent (Wt) | Functionality |
| Tragacanth gum or Locust bean gum | 15.0 | Thickener |
| Preservative | q.s. | |
| Water | 85.0 | |

To prepare this product, the preservative is added to the water and then the thickener gradually added while stirring on low speed using an Oster blender. The speed is increased to high until the material takes on the appearance of petroleum jelly. It is transferred to a suitable container by first heating to 55° C.

The synergistic composition is blended with a personal care or household products as exemplified above. Generally the total preservative present will be from 0.01 to 1.0% by weight, most preferably from 0.01 to 0.4%.

In formulating the composition, naturally, the amount of the synergistic combination must be sufficient to be effective against the microorganisms which must be inhibited. Such minimum inhibitory concentrations can be readily determined by simple laboratory experimentation using standardized testing techniques.

In order to more fully illustrate the invention, attention is directed to the following examples:

EXAMPLES

To demonstrate the microbiological effects produced by the synergistic composition, a cream and a lotion formulation were prepared. The dimethyloldimethylhydantoin (DMDMH) and 3-iodo-2-propynylbutyl carbamate (IPBC) were added at various use levels and microbiological challenge tests were conducted.

The cream had the following composition:

| Ingredient | Percent by Weight |
|---|---|
| PEG-20 Glyceryl stearate | 4.0 |
| Glyceryl monostearate | 6.0 |
| Cetearyl alcohol (TA 16185) | 1.5 |
| Myristyl propionate | 8.0 |
| Glycerine, 99% | 5.0 |
| Water, deionized | 75.5 |

To prepare the cream, the oil phase was first solubilized at 60°-65° C. The water phase (glycerin and water) was heated to the same temperature and added to the oil phase with mixing. The temperature was maintained at 48°-52° C. and the preservative system was added. The product was cooled with stirring to room temperature.

The lotion had the following composition:

| Ingredient | Percent (W) | Functionality |
|---|---|---|
| Phase A | | |
| Stearic acid USP/NF | 3.0 | Emulsifier |
| Myristyl propionate | 2.0 | Emollient |
| Glyceryl monostearate | 1.5 | Emulsifier |
| Cetyl alcohol | 1.0 | Secondary emulsifier |
| Ethoxylated (5) lanolin alcohols | 0.5 | Emollient |
| Ethoxylated (25) lanolin alcohols | 0.3 | Emulsifier |
| Phase B | | |
| Hydrogenated starch hydrolysate | 5.0 | Humectant |
| Triethanolamine (99%) | 0.4 | Emulsifier |
| Preservative | q.s. | |
| Water, deionized | 85.3 | |
| Phase C | | |
| Hydrolyzed animal protein | 1.0 | Moisturizer |

To prepare the lotion (known as TEA stearate lotion), Phase A and Phase B were heated separately to 65° C. Phase C was then added to Phase A with mixing and the mixture added to Phase B at 60° C. The preservative was added at this latter temperature. If necessary, the pH of the mixture is adjusted to 7.0 with 50% acetic acid and the lotion cooled to room temperature with stirring to complete the formulation.

Microbiological challenge tests were carried out by first inoculating forty gram aliquots of the formulation containing various amounts of preservative with Candida albicans (ATCC NO. 10231) and Aspergillus niger (ATCC No. 16404) at concentrations of approximately $5 \times 10^6$ organisms per gram of formulation. The temperature of the samples was kept at 48°-52° C. where sample viscosity was sufficiently low to insure homogeneous distribution of organisms after inoculation. Samples were incubated at 18°-22° C. for a total of 7 days. A one ml. aliquot was taken from each sample on 0, 1, 2, 3 and 7 days, and diluted stepwise down to a 10!hu 6 reduction in concentration. Each diluted sample was plated out in mycophil agar medium and incubated for three to seven days at 20°-25° C. After incubation, readings of the number of colonies per milliliter (cfu/ml) were made from the 0 to 7 day samples. The data are presented in Tables 1 to 3.

TABLE 1

Synergistic Effects of DMDMH and IPBC
Candida Albicans in GMS Cream

| System No. | DMDMH % | IPBC % | Total Wt., % | Ratio DMDMH/IPBC | Counts 3 Days CFU |
|---|---|---|---|---|---|
| 30 | 0.00 | 0.00 | 0.00 | | 2,000,000 |
| 26 | 0.22 | 0.00 | 0.22 | | 600,000 |
| 5 | 0.00 | 0.0244 | 0.0244 | | 900 |
| 1 | 0.22 | 0.0244 | 0.2444 | 9.02 | <10 |
| 26 | 0.22 | 0.00 | 0.22 | | 600,000 |
| 10 | 0.00 | 0.0122 | 0.0122 | | 20,000 |
| 6 | 0.22 | 0.0122 | 0.2322 | 18.03 | <10 |
| 26 | 0.22 | 0.00 | 0.22 | | 600,000 |
| 15 | 0.00 | 0.0061 | 0.0061 | | 500,000 |
| 11 | 0.22 | 0.0061 | 0.2261 | 36.06 | 200 |
| 26 | 0.22 | 0.00 | 0.22 | | 600,000 |
| 20 | 0.00 | 0.0030 | 0.0030 | | 700,000 |
| 16 | 0.22 | 0.0030 | 0.2230 | 73.33 | 2,000 |
| 27 | 0.165 | 0.00 | 0.165 | | 2,000,000 |
| 5 | 0.00 | 0.0244 | 0.0244 | | 900 |
| 2 | 0.165 | 0.0244 | 0.1894 | 6.76 | <10 |
| 27 | 0.165 | 0.00 | 0.165 | | 2,000,000 |
| 10 | 0.00 | 0.0122 | 0.0122 | | 20,000 |
| 7 | 0.165 | 0.0122 | 0.1772 | 13.52 | <10 |
| 27 | 0.165 | 0.00 | 0.165 | | 2,000,000 |
| 15 | 0.00 | 0.0061 | 0.0061 | | 500,000 |
| 12 | 0.165 | 0.0061 | 0.1671 | 27.05 | 20 |
| 28 | 0.11 | 0.00 | 0.11 | | 900,000 |
| 5 | 0.00 | 0.0244 | 0.0244 | | 900 |
| 3 | 0.11 | 0.0244 | 0.1344 | 4.51 | <10 |
| 28 | 0.11 | 0.00 | 0.11 | | 900,000 |
| 10 | 0.00 | 0.0122 | 0.0122 | | 20,000 |
| 8 | 0.11 | 0.0122 | 0.1222 | 9.02 | <10 |
| 28 | 0.11 | 0.00 | 0.11 | | 900,000 |
| 15 | 0.00 | 0.0061 | 0.0061 | | 500,000 |
| 13 | 0.11 | 0.0061 | 0.1161 | 18.03 | 1,100 |
| 28 | 0.11 | 0.00 | 0.11 | | 900,000 |
| 20 | 0.00 | 0.0030 | 0.0030 | | 700,000 |
| 18 | 0.11 | 0.0030 | 0.1130 | 36.66 | 8,000 |
| 29 | 0.055 | 0.00 | 0.055 | | 4,000,000 |
| 5 | 0.00 | 0.0244 | 0.0244 | | 900 |
| 4 | 0.055 | 0.0244 | 0.794 | 2.25 | <10 |
| 29 | 0.055 | 0.00 | 0.055 | | 4,000,000 |
| 10 | 0.00 | 0.0122 | 0.0122 | | 20,000 |
| 9 | 0.055 | 0.0122 | 0.0672 | 4.51 | <10 |
| 29 | 0.055 | 0.00 | 0.055 | | 4,000,000 |
| 15 | 0.00 | 0.0061 | 0.0061 | | 500,000 |
| 14 | 0.055 | 0.0061 | 0.0611 | 9.02 | 200 |

TABLE 2

Synergistic Effects of DMDMH and IPBC
Candida Albicans in TEA Stearate Lotion

| System No. | DMDMH % | IPBC % | Total Wt., % | Ratio DMDMH/IPBC | Counts 3 Days CFU |
|---|---|---|---|---|---|
| 7 | 0.00 | 0.0000 | 0.000 | | 7,000,000 |
| 8 | 0.22 | 0.0000 | 0.2200 | | 2,000 |
| 11 | 0.00 | 0.0122 | 0.0122 | | 20,000 |
| 1 | 0.22 | 0.0122 | 0.2322 | 18.03 | <10 |
| 8 | 0.22 | 0.0000 | 0.2200 | | 2,000 |
| 12 | 0.00 | 0.0061 | 0.0061 | | 40,000 |
| 2 | 0.22 | 0.0061 | 0.2261 | 36.06 | <10 |
| 9 | 0.165 | 0.0000 | 0.165 | | 4,000,000 |
| 11 | 0.00 | 0.0122 | 0.0122 | | 20,000 |
| 3 | 0.165 | 0.0122 | 0.1772 | 13.52 | <10 |
| 9 | 0.165 | 0.0000 | 0.165 | | 4,000,000 |
| 12 | 0.00 | 0.0061 | 0.0061 | | 40,000 |
| 4 | 0.165 | 0.0061 | 0.1711 | 27.05 | <10 |
| 10 | 0.11 | 0.0000 | 0.11 | | 7,000,000 |
| 11 | 0.00 | 0.0122 | 0.0122 | | 20,000 |
| 5 | 0.11 | 0.0122 | 0.1222 | 9.02 | <10 |
| 10 | 0.11 | 0.0000 | 0.11 | | 7,000,000 |
| 12 | 0.00 | 0.0061 | 0.0061 | | 40,000 |
| 6 | 0.11 | 0.0061 | 0.1161 | 18.03 | <10 |

TABLE 3

Synergistic Effects of DMDMH and IPBC
Aspergillus Niger in GMS Cream

| System No. | DMDMH % | IPBC % | Total Wt., % | Ratio DMDMH/ IPBC | Counts 1 Day CFU |
|---|---|---|---|---|---|
| 30 | 0.00 | 0.00 | 0.00 | | 200,000 |
| 28 | 0.11 | 0.00 | 0.11 | | 30,000 |
| 5 | 0.00 | 0.0244 | 0.0244 | | 3,000,000 |
| 3 | 0.11 | 0.0244 | 0.1344 | 4.51 | <10 |
| 28 | 0.11 | 0.00 | 0.11 | | 30,000 |
| 10 | 0.00 | 0.0122 | 0.0122 | | 700,000 |
| 8 | 0.11 | 0.0122 | 0.1222 | 9.02 | <10 |

It will be noted from the above tables that the synergistic combination of the invention is considerably better than either of the compounds with regard to the microorganisms tested.

What is claimed is:

1. A preservative composition which comprises an admixture of (a) a nontoxic, nonodiferous formaldehyde donor and (b) a halopropynyl compound selected from iodopropargyl esters, ethers, acetals, carbamates and carbonates, wherein the weight ratio of component (a) to (b) is from 50:1 to 1:1.

2. The composition of claim 1 wherein the admixture contains dimethyloldimethylhydantoin and 3-iodo-2-propynylbutyl carbamate.

3. The composition of claim 1 wherein component (b) is 3-iodo-2-propynylbutyl carbamate.

4. The preservative composition of claim 1 wherein component (a) is dimethyloldimethylhydantoin; N,N''-methylene bis[N'-[1-(hydroxymethyl)-2,5-dioxo-4-imidazolidinyl]urea]; N-(hydroxymethyl)-N-(1,3-dihydroxymethyl-2,5-dioxo-4-imidazolidinyl)-N'-(hydroxymethyl) urea; or the cis isomer of 1-(3-chloroallyl)-3,5,5-triaza-1-azoniaadamantane chloride.

5. The composition of claim 1 wherein the weight ratio of component (a) to (b) is from 20:1 to 10:1.

6. A personal care composition which comprises a surface active agent containing an effective amount of the composition of claim 1.

7. The personal care composition of claim 6 wherein the composition is a skin cream, a lotion, a shampoo, or a soap.

8. A household product composition which comprises a surface active agent containing an effective amount of the composition of claim 1.

9. The household product composition of claim 8 wherein the composition is a detergent, a hard surface cleaner, a fabric softener, or a room deodorizer.

10. A method of inhibiting the growth of microorganisms which comprises contacting said organisms with the composition of claim 1.

* * * * *